(12) United States Patent
Hares

(10) Patent No.: US 11,992,285 B2
(45) Date of Patent: May 28, 2024

(54) DETECTING COLLISIONS OF ROBOT ARMS

(71) Applicant: CMR SURGICAL LIMITED, Cambridge (GB)

(72) Inventor: Luke David Ronald Hares, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 776 days.

(21) Appl. No.: 17/255,564

(22) PCT Filed: Jun. 27, 2019

(86) PCT No.: PCT/GB2019/051819
§ 371 (c)(1),
(2) Date: Dec. 23, 2020

(87) PCT Pub. No.: WO2020/002922
PCT Pub. Date: Jan. 2, 2020

(65) Prior Publication Data
US 2021/0267700 A1    Sep. 2, 2021

(30) Foreign Application Priority Data

Jun. 29, 2018 (GB) .................................... 1810754

(51) Int. Cl.
*A61B 34/00* (2016.01)
*A61B 34/37* (2016.01)
(Continued)

(52) U.S. Cl.
CPC .............. *A61B 34/70* (2016.02); *A61B 34/37* (2016.02); *B25J 9/0084* (2013.01); *B25J 9/0087* (2013.01);
(Continued)

(58) Field of Classification Search
CPC ......... A61B 34/70; A61B 34/37; A61B 34/30; A61B 34/74; A61B 2034/2059;
(Continued)

(56) References Cited

U.S. PATENT DOCUMENTS 10,145,747 B1\* 12/2018 Lin .................. A61B 90/06
10,690,558 B2\* 6/2020 Nakata ................. G01L 5/226
(Continued)

FOREIGN PATENT DOCUMENTS

CN 105751222 A 7/2016
CN 107427328 A 12/2017
(Continued)

OTHER PUBLICATIONS

Anonymous: "Robot kinematics—Wikipedia", Apr. 14, 2018 (Apr. 14, 2018), XP055624232, Retrieved from the Internet: URL:https://en.wikipedia.org/w/index.php?title=Robot_kinematics&oldid=836405034.
(Continued)

*Primary Examiner* — Peter D Nolan
*Assistant Examiner* — Michael F Whalen
(74) *Attorney, Agent, or Firm* — Lando & Anastasi, LLP

(57) ABSTRACT

A robotic system comprises two robots and a control unit. Each robot has a base and an arm extending from the base to an attachment for an instrument. Each arm comprises a plurality of joints whereby the configuration of the arm can be altered. Each robot comprises a driver for each joint configured to drive the joint to move, and position and torque sensors. The control unit controls the drivers in dependence on inputs from the sensors. The control unit: determines the gravitational torques on the joints of the arms of the robots in the arm configurations indicated from the inputs from the position sensors; from the inputs from the torque sensors and the determined gravitational torques,
(Continued)

determines residual torques on the joints of the arms of the robots in the indicated arm configurations; calculate a candidate force for each arm which when applied to that arm would cause the determined residual torques; and determines a collision if a candidate force on the arm of the first robot balances an opposing candidate force on the arm of the second robot.

20 Claims, 8 Drawing Sheets

(51) Int. Cl.
    *B25J 9/00*         (2006.01)
    *B25J 9/16*         (2006.01)

(52) U.S. Cl.
    CPC ........... *B25J 9/1633* (2013.01); *B25J 9/1676* (2013.01); *B25J 9/1682* (2013.01); *B25J 9/1697* (2013.01)

(58) Field of Classification Search
    CPC ...... B25J 9/0084; B25J 9/0087; B25J 9/1633; B25J 9/1676; B25J 9/1682; B25J 9/1697; B25J 9/1674; G05B 2219/39082; G05B 2219/39089; G05B 2219/39091; G05B 2219/39109; G05B 2219/40205
    See application file for complete search history.

(56) References Cited

U.S. PATENT DOCUMENTS

| | | |
|---|---|---|
| 2003/0139733 A1 | 7/2003 | Wang et al. |
| 2013/0073085 A1 | 3/2013 | Oaki et al. |
| 2015/0104284 A1* | 4/2015 | Riedel ..................... B25J 15/00 414/738 |
| 2016/0193731 A1 | 7/2016 | Sattler et al. |
| 2017/0189126 A1* | 7/2017 | Weir ...................... A61B 34/25 |
| 2018/0036090 A1 | 2/2018 | Hasegawa et al. |
| 2018/0164170 A1* | 6/2018 | Nakata ................... B25J 9/1674 |

FOREIGN PATENT DOCUMENTS

| | | |
|---|---|---|
| CN | 115334996 A | 11/2022 |
| EP | 3017920 A1 | 5/2016 |
| JP | H10329071 A | 12/1998 |
| WO | WO-2019074669 A1 * | 4/2019 ......... A61B 1/00006 |

OTHER PUBLICATIONS

Filippo D'ippolito et al.: "Contact Estimation in Robot Interaction", International Journal of Advanced Robotic Systems, vol. 11, Jan. 1, 2014 (Jan. 1, 2014), pp. 1-10, XP055303197, ISSN: 1729-8806, DOI: 10.5772/58688.

Notification of Transmittal of the International Search Report and the Written Opinion of the International Searching Authority from corresponding PCT/GB2019/051819 dated Sep. 27, 2019.

United Kingdom Search Report from corresponding United Kingdom Application No. GB1810754.0 dated Dec. 24, 2018.

Japanese Notification of Reasons for Refusal from corresponding Japanese Application No. 2020-573161 dated Feb. 8, 2022.

A. De Luca, A. Albu-Schaffer, S. Haddadin and G. Hirzinger, "Collision Detection and Safe Reaction with the DLR-III Lightweight Manipulator Arm," 2006 IEEE/RSJ International Conference on Intelligent Robots and Systems, 2006, pp. 1623-1630, doi: 10.1109/IROS.2006.282053.

Australian Examination Report No. 1 from corresponding Australian Application No. 2019295378 dated Feb. 21, 2022.

Indian Examination Report from corresponding Indian Application No. 202117003495 dated Jan. 6, 2022.

Chinese Notice of First Office Action from corresponding Chinese Application No. 201980044134.4 dated Sep. 21, 2023.

* cited by examiner

DETECTING COLLISIONS OF ROBOT ARMS

CROSS-REFERENCE TO RELATED APPLICATIONS

This application is a U.S. National Phase Application under 35 U.S.C. § 371 of International Application No. PCT/GB2019/051819, filed Jun. 27, 2019, which claims priority to United Kingdom Application No. 1810754.0, filed Jun. 29, 2018. Each application referenced above is hereby incorporated by reference in its entirety for all purposes.

BACKGROUND

This disclosure relates to controlling the motion of robots, in particular surgical robots.

FIG. 1 illustrates multiple robots 101, 102, 103 operating in a common workspace. In this example, the robots are surgical robots being used to perform an operation on a person 104. Each robot comprises a base connected to a surgical instrument via a flexible arm. The robots are controlled remotely, in this case by a surgeon. The surgeon is located at a surgeon console 200, shown in FIG. 2. The surgeon manipulates hand controllers 201, 202. A control system converts the movement of the hand controllers into control signals to move the arm joints and/or instrument end effector of a surgical robot. More than one robot may move at the same time.

Operating robot arms in a common workspace leads to a risk of those robot arms colliding with each other. This is particularly likely in a compact common workspace where the operational area of one robot significantly overlaps the operational area of another robot. In master-slave manipulator systems, such as the surgeon-robot system described above, the likelihood of collision is increased since the movements of the robot arms are not pre-planned but executed in response to the surgeon's inputs.

In master-slave manipulator systems with multiple robots it is known to mount all the robots on a common chassis. In this case, the relative positions of the robot bases are known. Using sensory data, the pose of each robot arm can be determined. Thus, the position of each point on one robot arm can be determined relative to the position of each point on another robot arm. Using this information, the control system can detect an imminent collision of robot arms and modify the movement of the robot arms so as to prevent the collision.

In systems where the robots are not mounted to a common chassis, but instead are independently mounted, the position of one robot relative to another is not inherently known. If the relative positions of the robots are not otherwise determined, then the above mechanism cannot be used to detect and prevent collisions. Additionally, once a collision has occurred, the parts of the robot arms that have collided cannot be determined.

There is a need for a control system for detecting collisions of robot arms without requiring knowledge of the relative positions of the robot arms.

SUMMARY OF THE INVENTION

According to a first aspect, there is provided a robotic system comprising: a first robot and a second robot, each robot having a base, and an arm extending from the base to an attachment for an instrument, the arm comprising a plurality of joints whereby the configuration of the arm can be altered, for each joint the robot comprising a driver configured to drive the joint to move, and a position sensor and torque sensor configured to sense the joint; and a control unit configured to receive inputs from the position sensors and torque sensors, and to control the drivers in dependence on those received inputs, the control unit configured to: determine the gravitational torques on the joints of the arms of the first and second robots in the arm configurations indicated from the inputs from the position sensors; from the inputs from the torque sensors and the determined gravitational torques, determine residual torques on the joints of the arms of the first and second robots in the indicated arm configurations; calculate one or more candidate force for each arm which when applied to that arm would cause the determined residual torques; and determine a collision if one or more candidate force on the arm of the first robot balances an opposing candidate force on the arm of the second robot.

The control unit may, on determining a collision, control the drivers so as to prevent the arms of the first and second robot from moving.

The control unit may, on determining a collision, control the drivers to move the arms of the first and second robot away from the point of contact.

The control unit may control the drivers only if the candidate force exceeds a threshold force.

The control unit may control the drivers only if the temporal profile of the candidate force has a gradient greater than a threshold gradient.

The control unit may control the drivers only if the candidate force has a magnitude greater than a baseline value for a time period that is less than a threshold time period.

The robotic system may comprise further robots, each further robot having a base, and an arm extending from the base to an attachment for an instrument, the arm comprising a plurality of joints whereby the configuration of the arm can be altered, for each joint the robot comprising a driver configured to drive the joint to move, and a position sensor and torque sensor configured to sense the joint, the control unit configured to: determine the gravitational torques on the joints of the arms of the further robots in the arm configurations indicated from the inputs from the position sensors; from the inputs from the torque sensors and the determined gravitational torques, determine residual torques on the joints of the arms of the further robots in the indicated arm configurations; calculate one or more candidate force for each arm of the further robots which when applied to that arm would cause the determined residual torques; and control the drivers only if a collision is determined and the candidate force on the arm of the first robot which balances an opposing candidate force on the arm of the second robot does not also balance an opposing candidate force on the arm of a further robot.

The control unit may store the configuration of the arm of the first robot and the configuration of the arm of the second robot at the time of the determined collision, and subsequently prevent the first robot and the second robot from both adopting those stored configurations at the same time.

The control unit may determine the relative position of the arm of the first robot and the arm of the second robot from the determined collision, and subsequently prevent the arm of the first robot and the arm of the second robot from adopting the same relative position at the same time.

The control unit may operate without knowledge of the relative positions of the first robot and the second robot.

The control unit may assume that the first and second robots each adopt a predetermined orientation with respect to each other.

The control unit may calculate only a single candidate force for each arm which when applied to that arm would cause the determined residual torques.

The control unit may determine that no collision has taken place if there is no single candidate force which when applied to the arm of the first robot would cause the determined residual torques on the joints of the arm of the first robot in the indicated arm configuration.

The control unit may calculate only a single candidate force range for each arm which when applied to that arm would cause the determined residual torques.

The single candidate force range may comprise a candidate magnitude range and a candidate line of action range.

The control unit may determine that no collision has taken place if the candidate line of action range of the arm of the first robot does not overlap with the candidate line of action range of the arm of the second robot.

The control unit may determine that no collision has taken place if the candidate line of action range of the arm of the first robot does not include a line of action in an opposing direction to a line of action in the candidate line of action range of the arm of the second robot.

The control unit may determine that no collision has taken place if the candidate magnitude range of the arm of the first robot does not overlap with the candidate magnitude range of the arm of the second robot.

The control unit may determine, for each arm, a plurality of candidate forces, each of which when applied to that arm would cause the determined residual torques, the plurality of candidate forces including combination candidate forces, combination candidate forces being a combination of two or more individual candidate forces, the control unit being configured to determine a collision if an individual candidate force of a combination candidate force on the arm of the first robot balances an opposing candidate force on the arm of the second robot.

The robotic system may be a surgical robotic system, and the first and second robots may be surgical robots.

According to a second aspect, there is provided method of determining collisions between a first robot and a second robot of a robotic system, each robot having a base, and an arm extending from the base to an attachment for an instrument, the arm comprising a plurality of joints whereby the configuration of the arm can be altered, for each joint the robot comprising a driver configured to drive the joint to move, and a position sensor and torque sensor configured to sense the joint, the robotic system further comprising a control unit for receiving inputs from the position sensors and torque sensors and for controlling the drivers in dependence on those received inputs, the method comprising: determining the gravitational torques on the joints of the arms of the first and second robots in the arm configurations indicated from the inputs from the position sensors; from the inputs from the torque sensors and the determined gravitational torques, determining residual torques on the joints of the arms of the first and second robots in the indicated arm configurations; calculating one or more candidate force for each arm which when applied to that arm would cause the determined residual torques; and determining a collision if one or more candidate force on the arm of the first robot balances an opposing candidate force on the arm of the second robot.

BRIEF DESCRIPTION OF THE DRAWINGS

The present disclosure will now be described by way of example with reference to the accompanying drawings. In the drawings.

DETAILED DESCRIPTION

The following description relates to a robotic system comprising a plurality of robots and a control unit. The control unit drives the robots to move. Position and torque sensors on the robot arms relay sensory data to the control unit. The control unit uses this sensory data to detect external forces acting on the robot arms. If an external force acting on one arm balances an opposing external force acting on another arm, the control unit determines a collision has occurred between those two arms.

Figure 1:
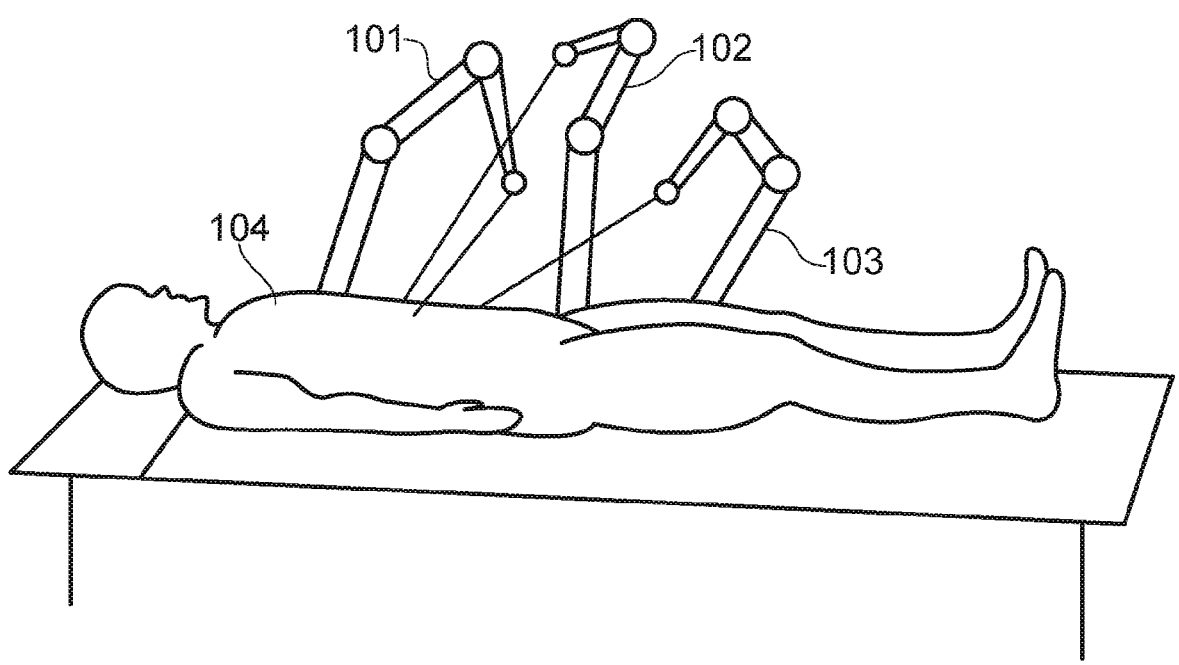
FIG. 1 illustrates a person being operated on by a robotic system comprising three surgical robots.
Figure 2:
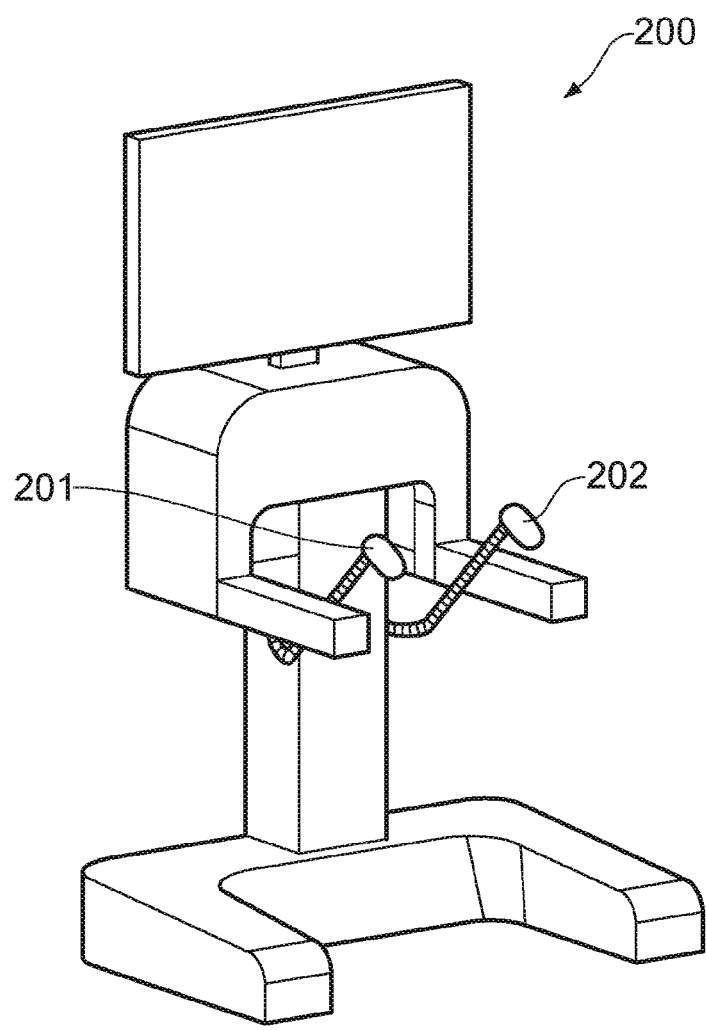
FIG. 2 illustrates a surgeon's console.
Figure 3:
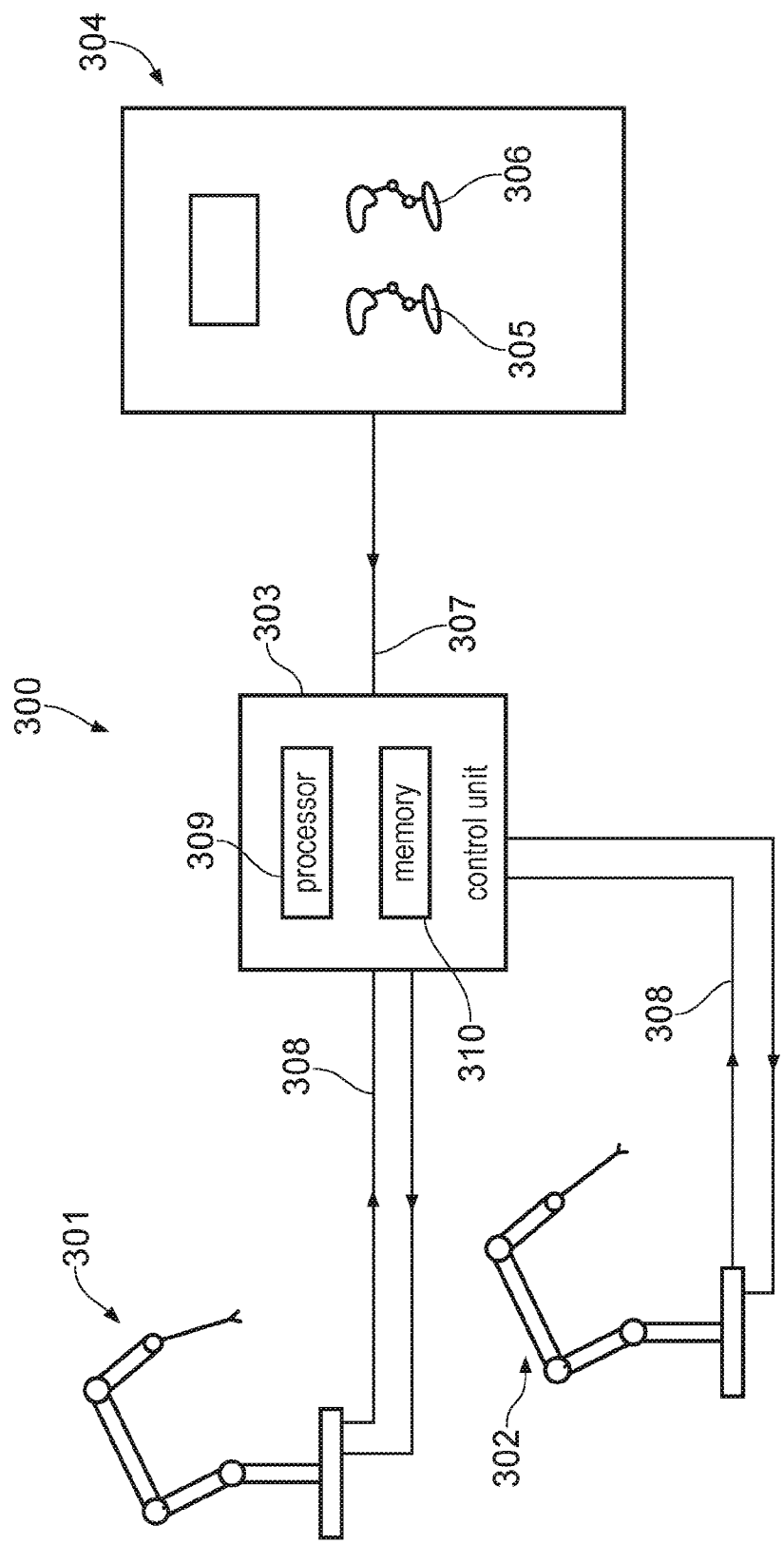
FIG. 3 illustrates a schematic diagram of a robotic system.

The following examples relate to a surgical robotic system. With reference to FIG. 3, the surgical robotic system 300 comprises two surgical robots 301, 302 driven by a control unit 303. The control unit 303 receives inputs 307 from a surgeon's console 304, including inputs from first and second hand controllers 305, 306. The control unit may receive other inputs 307 from the surgeon's console, such as foot pedal(s) inputs, button inputs, voice recognition inputs, gesture recognition inputs, eye recognition inputs etc. The control unit 303 also receives inputs 308 from the surgical robots 301, 302. These inputs include sensory data from position sensors and torque sensors located on the robot arm joints. The control unit 303 may receive other inputs 308 from each robot, such as force feedback, data from the surgical instrument etc. The control unit 303 drives the robots 301, 302 in response to the inputs it receives from the robots and the surgeon's console. The control unit 303 comprises a processor 309 and a memory 310. The memory stores, in a non-transient way, software code that can be executed by the processor to cause the processor to control the drivers in the manner described herein.

Figure 4:
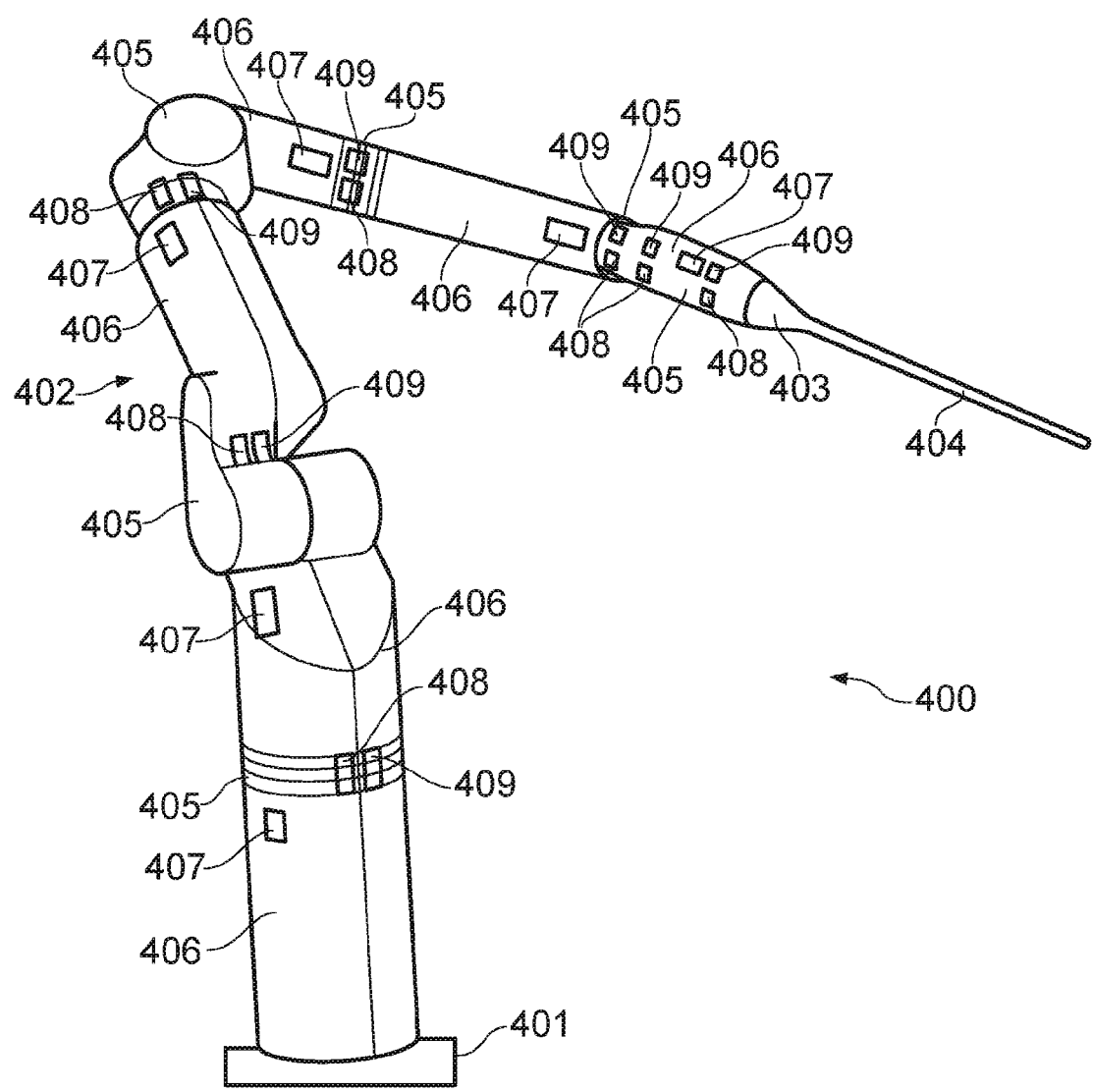
FIG. 4 illustrates a robot.

Each robot 301, 302 is of the form 400 illustrated in FIG. 4. The robot comprises a base 401 which is fixed in place when a surgical procedure is being performed. Suitably, the base 401 is mounted to a chassis. That chassis may be a cart, for example a bedside cart for mounting the robot at bed height. Alternatively, the chassis may be a ceiling mounted device, or a bed mounted device.

An arm 402 extends from the base 401 of the robot to an attachment 403 for a surgical instrument 404. The arm is flexible. It is articulated by means of multiple flexible joints 405 along its length. In between the joints are rigid arm members 406. The arm in FIG. 4 has seven joints. The joints include one or more roll joints (which have an axis of rotation along the longitudinal direction of the arm members on either side of the joint), one or more pitch joints (which have an axis of rotation transverse to the longitudinal direction of the preceding arm member), and one or more yaw joints (which also have an axis of rotation transverse to the longitudinal direction of the preceding arm member and also transverse to the rotation axis of a co-located pitch joint). However, the arm could be jointed differently. For example, the arm may have fewer or more joints. The arm may include joints that permit motion other than rotation between respective sides of the joint, for example a telescopic joint. The robot comprises a set of drivers 407, each driver 407 drives one or more of the joints 405.

The attachment 403 enables the surgical instrument 404 to be releasably attached to the distal end of the arm. The surgical instrument 404 has a linear rigid shaft and a working tip at the distal end of the shaft. The working tip comprises an end effector for engaging in a medical procedure. The surgical instrument may be configured to extend linearly parallel with the rotation axis of the terminal joint of the arm. For example, the surgical instrument may extend along an axis coincident with the rotation axis of the terminal joint of the arm. The surgical instrument 404 could be, for example, a cutting, grasping, cauterising or imaging device.

The robot arm comprises a series of sensors 408, 409. These sensors comprise, for each joint, a position sensor 408 for sensing the position of the joint, and a torque sensor 409 for sensing the applied torque about the joint's rotation axis. One or both of the position and torque sensors for a joint may be integrated with the motor for that joint. The outputs of the sensors are passed to the control unit 303 where they form inputs for the processor 309.

The following describes examples in which the control unit 303 utilises the sensory data received from the robots 301, 302 in order to detect a collision between the arms of the robots.

Figure 5:
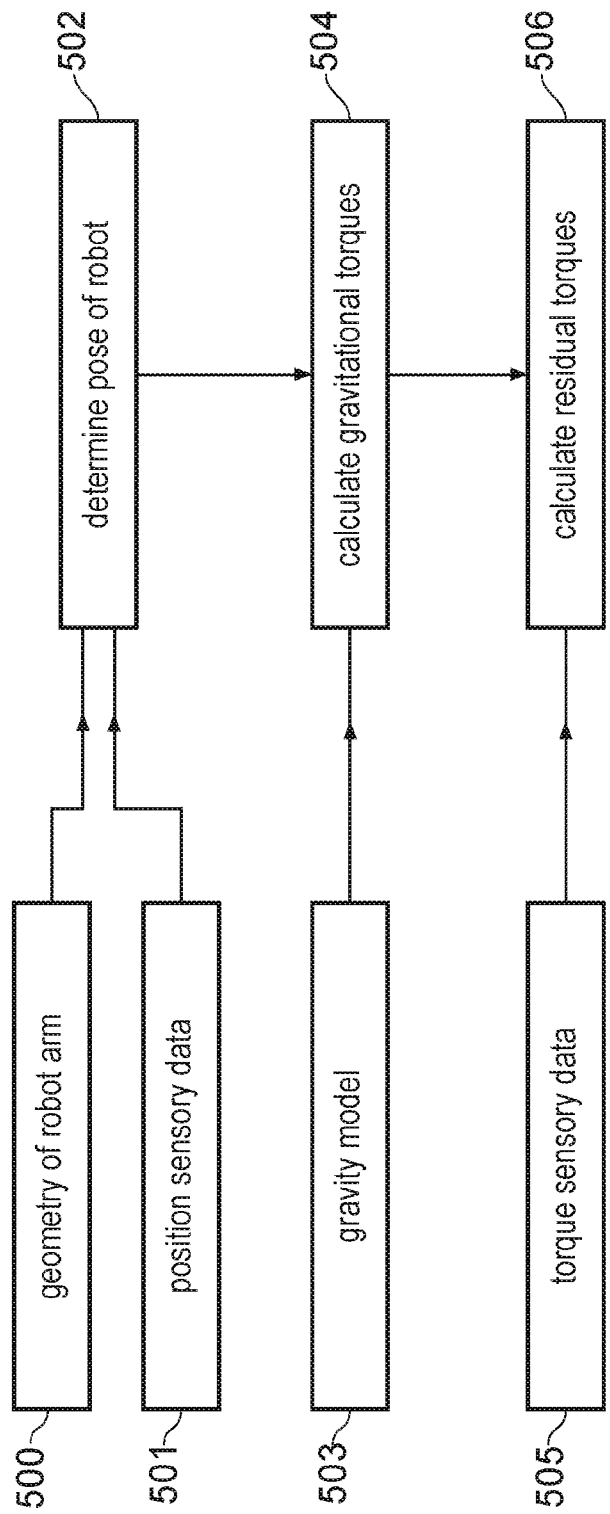
FIG. 5 is a flowchart showing the process of determining residual torques acting on a robot arm.

Firstly, for each robot arm, the control unit determines whether there is a force acting on that robot arm which is unaccounted for. FIG. 5 is a flowchart illustrating steps implemented by the control unit 303 to do this.

The control unit receives as an input position sensory data 501 from the position sensors 408 on the joints of the robot arm. For example, each position sensor may report the joint angle of the joint it is sensing. The control unit stores the geometry/layout of the robot arm 500 in memory 310. The processor 309 of the control unit retrieves the stored geometry of the robot arm from memory 310. At step 502, the processor 309 of the control unit determines the current configuration of the robot arm from the received position sensory data and the geometry of the robot arm. The configuration of the robot arm is also known as the pose of the robot arm. Suitably, the processor 309 stores the current configuration of the arm in memory 310.

The control unit stores a gravity model 503 of the robot arm in memory 310. The memory 310 stores for each element of the arm and the attached instrument, its mass, distance of its centre of mass from the preceding joint of the arm, and the relationship between the centre of mass and the positional output of the joint sensor for the preceding joint. The processor 309 of the control unit retrieves the stored gravity model 503 from the memory 310. At step 504, the processor 309 of the control unit uses the current configuration of the robot arm and the gravity model to model the effect of gravity on the elements of the robot arm for the current configuration of the robot arm. In doing this, the processor 309 determines the torque due to gravity acting on each joint of the robot arm.

The control unit receives as an input torque sensory data 505 from the torque sensors 409 on the joints of the robot arm. At step 506, the processor 309 of the control unit calculates the residual torque on each joint of the robot arm. The residual torque is the joint torque measured by the torque sensor from which known torque(s) acting on the joint have been deducted. For example, the processor 309 may calculate the residual torque by deducting the torque due to gravity calculated at step 504 from the measured joint torque. If the control unit was driving the joint to move under the control of the surgeon's console, then the processor 309 may deduct the known driven torque value from the measured joint torque in determining the residual torque. Suitably, the processor 309 stores the residual joints torques in memory 310.

It is not required for the control unit to actually determine the pose of the robot arm. The control unit may calculate the gravitational torques directly from the position sensory data, known geometry of the robot arm, and gravity model.

It is not required for the control unit to actually determine the gravitational torques acting on each joint of the robot arm. The control unit may calculate the residual torques directly from the position sensory data, known geometry of the robot arm, gravity model and torque sensory data.

The control unit performs the steps described in connection with FIG. 5 for all the robot arms to which it is connected.

By analysing the residual torques acting on the joints of the arms of the robots, the control unit 303 determines whether those residual torques could have been caused partially or entirely by the robots colliding. The control unit does this without knowledge of the relative positions of the robots. The control unit does, however, assume that the robots adopt a predetermined orientation with respect to each other. Alternatively, the relative orientation of the robots in the system may be input to the control unit prior to the control unit determining whether the robots have collided. For example, when the robots are setup prior to the beginning of the operation, the relative orientation of the robots may be provided to the control unit.

Some examples of how the control unit 303 may analyse the residual torques acting on the robot arm joints in order to determine whether a collision between two robot arms has taken place will now be described.

Figure 6A:
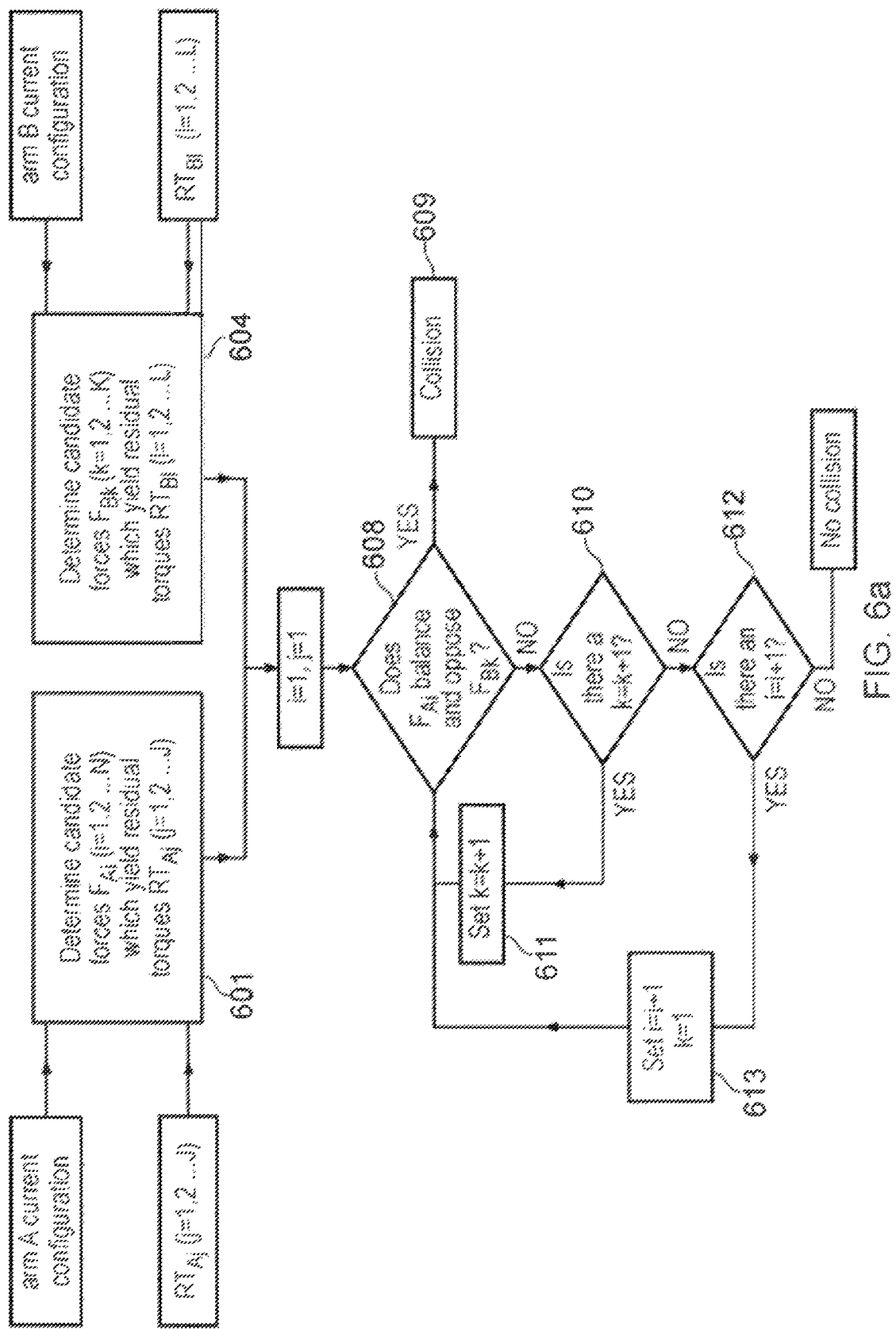
FIGS. 6a, 6b and 6c are collision analysis flowcharts.

FIG. 6a illustrates a first example implementation, concerning a robot arm A and a robot arm B. The residual joint torques calculated for arm A are denoted by RTAj (j=1, 2 . . . J). The residual joint torques for arm B are denoted by RTBl (l=1, 2 . . . L).

The control unit retrieves the current configuration of arm A from memory 310. It also retrieves the residual joint torques RTAj for arm A from memory 310. At step 601, the control unit 303 determines a set of candidate forces FAi (i=1, 2 . . . N) which would yield the residual joint torques RTAj in the current configuration of arm A.

The control unit retrieves the current configuration of arm B from memory 310. It also retrieves the residual joint torques RTBl for arm B from memory 310. At step 604, the control unit 303 determines a set of candidate forces FBk (k=1, 2 . . . K) which would yield the residual joint torques RTBl in the current configuration of arm B.

The candidate forces are forces applied externally to the arm in question. The set of candidate forces may include only one candidate force. The set of candidate forces may include individual candidate forces. In other words, the control unit may determine a single external force which alone would cause all of the residual joint torques of the arm. The set of candidate forces may include combination candidate forces. In other words, the control unit may determine two or more external forces, which together would cause all of the residual joint torques of the arm. The set of candidate forces may include an individual candidate force and a combination candidate force. The set of candidate forces may include all the external forces which could have been applied to the arm to cause the residual joint torques of the arm.

At step 608, the control unit compares the candidate forces FAi and FBk, where i=1, k=1. In other words, the control unit compares the first candidate force of arm A FA1 to the first candidate force of arm B FB1. If the compared candidate forces are balanced and opposed, then the control unit determines that arm A has collided with arm B at step 609. Specifically, the control unit may compare the magnitudes, lines of action, and directions of lines of action of the candidate forces FA1 and FB1. If the magnitudes of the forces are equal and acting on parallel lines in opposite directions, then the control unit determines a collision has happened between arm A and arm B.

If at step 608, the control unit determines that candidate forces FA1 and FB1 are not balanced and opposed, then no collision is detected. At step 610, the control unit looks to see if there is a further candidate force in the set of candidate forces for arm B. In other words, it looks to see if there is a k=k+1 force. If there is a further candidate force, then at step 611, k is set to k+1, and the analysis returns to step 608. This time, the control unit compares the candidate forces FAi and FBk+1, in other words FA1 and FB2. If these two candidate forces are balanced and opposed, then the control unit determines that arm A has collided with arm B.

If at step 608, the control unit determines that candidate forces FA1 and FB2 are not balanced and opposed, then no collision is detected and a further iteration of steps 610, 611 and 608 occurs. These iterations continue until either candidate force FA1 has been assessed against all the candidate forces FBk, or a collision has been detected.

If at step 610, the control unit determines that there are no further candidate forces for arm B, then the process continues to step 612. At step 612, the control unit looks to see if there is a further candidate force in the set of candidate forces for arm A. In other words, it looks to see if there is a i=i+1 force. If there is a further candidate force, then at step 613, i is set to i+1 and k is set to 1. The analysis then returns to step 608. This time, the control unit compares the candidate forces FAi+1 and FBk, in other words FA2 and FB1. If these two candidate forces are balanced and opposed, then the control unit determines that arm A has collided with arm B.

If at step 608, the control unit determines that candidate forces FA2 and FB1 are not balanced and opposed, then no collision is detected and a further iteration of steps 610, 611 and 608 occurs. These iterations continue until either candidate force FA2 has been assessed against all the candidate forces FBk, or a collision has been detected.

The remaining candidate forces for arm A are similarly compared against the candidate forces for arm B in the manner described above. If any of the candidate forces of arm A FAi balance and oppose any of the candidate forces of arm B FBk, then the control unit 303 determines a collision. If none of the candidate forces of arm A FAi balance and oppose a candidate force of arm B FBk, then the control unit 303 determines that no collision has occurred.

The control unit 303 may stop the analysis of FIG. 6a as soon as a collision is determined, i.e. as soon as a pair of candidate forces are identified which balance and oppose each other. Alternatively, the control unit 303 may compare each candidate force of arm A with each candidate force of arm B, independently of whether a collision has been detected.

When a collision is determined, the control unit may store the candidate forces of arm A and B which balanced and opposed each other in the memory 310. The control unit may also store the configurations of both arms A and B at the time of the collision in memory 310.

This collision analysis accurately detects a collision of robot arms, even if that collision occurred at the same time that other external force(s) were acting on one or both of the colliding robot arms.

Figure 6B:
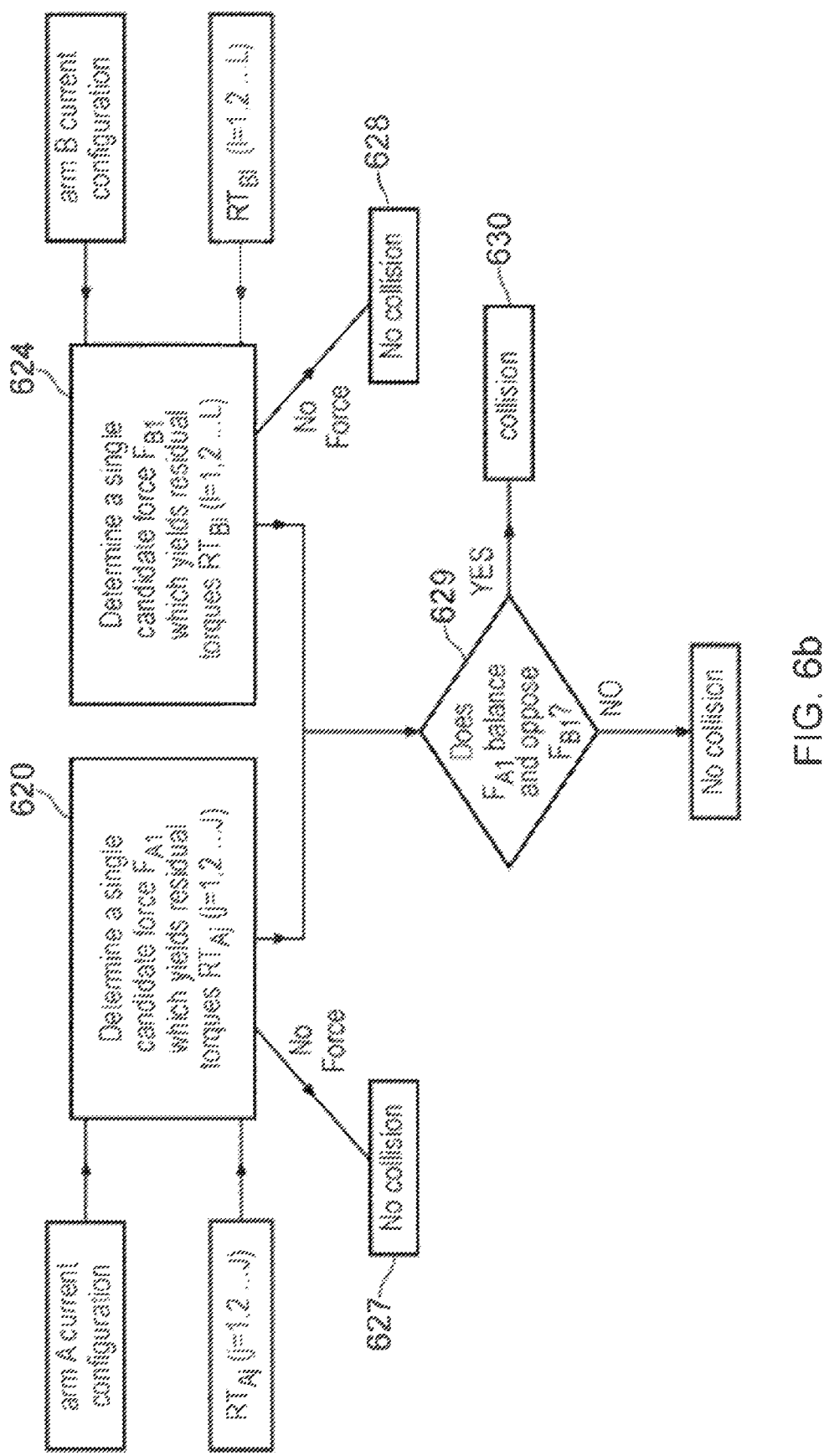

FIG. 6b illustrates a second example implementation, concerning a robot arm A and a robot arm B. As with FIG. 6a, the residual joint torques calculated for arm A are denoted by RTAj (j=1, 2 . . . J). The residual joint torques for arm B are denoted by RTBl (l=1, 2 . . . L).

The control unit is configured to assume that a single external force only caused the residual joint torques on arm A. Similarly, the control unit is configured to assume that a single external force only caused the residual joint torques on arm B. Thus, the control unit is configured to calculate only a single candidate force for each arm which when applied to that arm would cause the residual joint torques. The single candidate force is an individual candidate force not a combination candidate force.

The control unit retrieves the current configuration of arm A from memory 310. It also retrieves the residual joint torques RTAj for arm A from memory 310. At step 620, the control unit 303 determines a single candidate force FA1 which would yield the residual joint torques RTAj in the current configuration of the arm A. If no single candidate force FA1 can be determined, then at step 627, the control unit determines that no collision has occurred.

The control unit retrieves the current configuration of arm B from memory 310. It also retrieves the residual joint torques RTBl for arm B from memory 310. At step 624, the control unit 303 determines a single candidate force FB1 which would yield the residual joint torques RTBl in the current configuration of the arm B. If no single candidate force FB1 can be determined, then at step 628, the control unit determines that no collision has occurred.

If a candidate force FA1 and a candidate force FB1 are determined at steps 620 and 624, then at step 629, the control unit compares FA1 and FB1. If the compared candidate forces are balanced and opposed, then the control unit determines that arm A has collided with arm B at step 630. Specifically, the control unit may compare the magnitudes, lines of action, and directions of lines of action of the candidate forces FA1 and FB1. If the magnitudes of the forces are equal and acting on parallel lines in opposite directions, then the control unit determines a collision has happened between arm A and arm B.

If at step 629, the control unit determines that candidate forces FA1 and FB1 are not balanced and opposed, then no collision is detected.

Compared to the collision analysis described with respect to FIG. 6a, the collision analysis described with respect to FIG. 6b is less computationally intense.

Figure 6C:
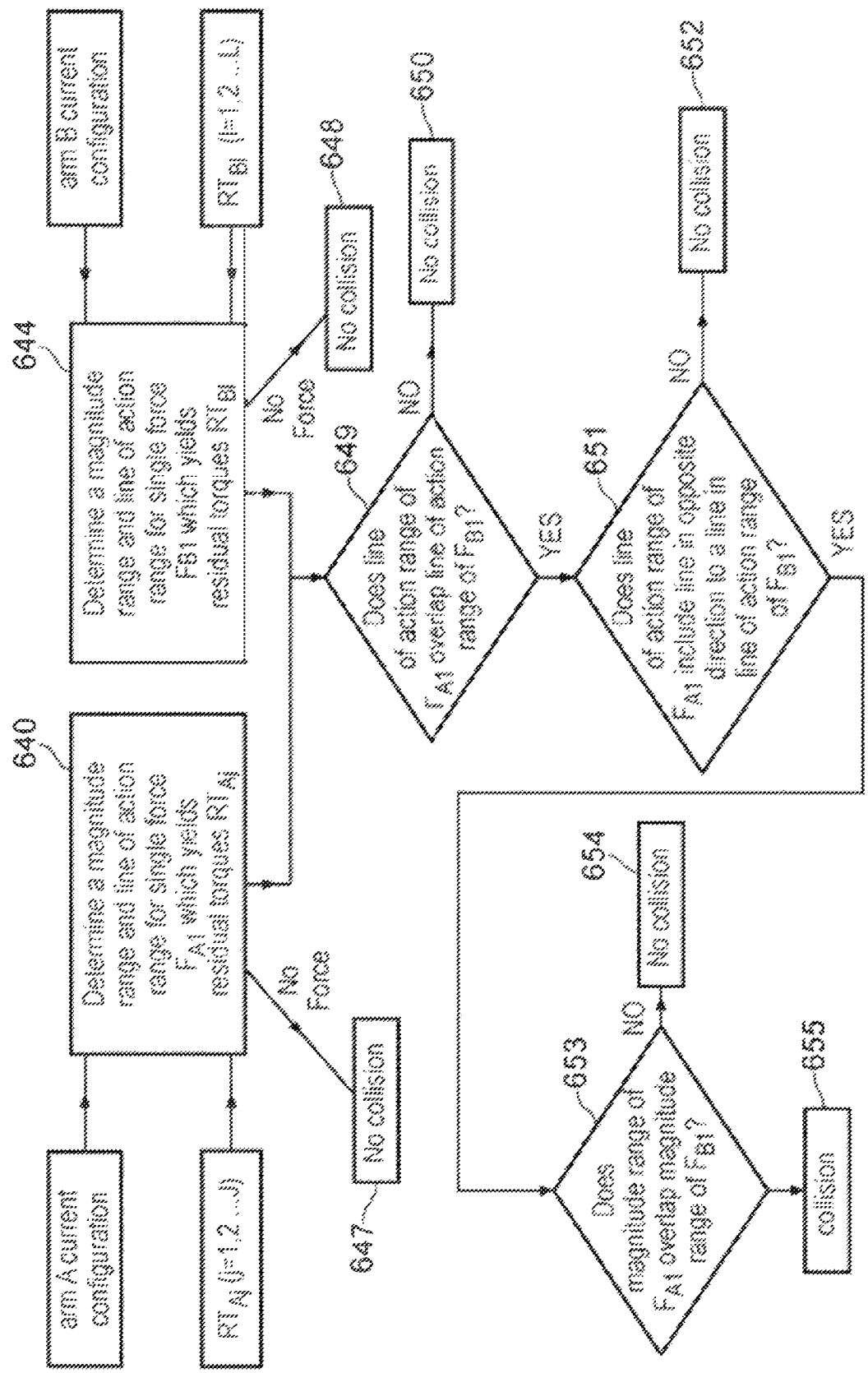

FIG. 6c illustrates a third example implementation, concerning a robot arm A and a robot arm B. As with FIGS. 6a and 6b, the residual joint torques calculated for arm A are denoted by RTAj (j=1, 2 . . . J). The residual joint torques for arm B are denoted by RTBl (l=1, 2 . . . L).

The control unit is configured to assume that a single external force only caused the residual joint torques on arm A. Similarly, the control unit is configured to assume that a single external force only caused the residual joint torques on arm B. The control unit is configured to calculate a range of magnitudes and a range of lines of action for a single candidate force which when applied to that arm would cause the residual joint torques. The single candidate force is an individual candidate force not a combination candidate force.

The control unit retrieves the current configuration of arm A from memory 310. It also retrieves the residual joint torques RTAj for arm A from memory 310. At step 640, the control unit 303 determines a magnitude range and a line of action range for a single candidate force FA1 which would yield the residual joint torques RTAj in the current configuration of arm A. If no single candidate magnitude range and line of action range for force FA1 can be determined, then at step 647, the control unit determines that no collision has occurred.

The control unit retrieves the current configuration of arm B from memory 310. It also retrieves the residual joint torques RTBl for arm B from memory 310. At step 644, the control unit 303 determines a magnitude range and a line of action range for a single candidate force FB1 which would yield the residual joint torques RTBl in the current configuration of arm B. If no single candidate magnitude range and line of action range for force FB1 can be determined, then at step 648, the control unit determines that no collision has occurred.

If a candidate magnitude range and a candidate line of action range for force FA1 and a candidate magnitude range and a candidate line of action range for force FB1 are determined at steps 640 and 644, then the analysis moves on to step 649. At step 649, the control unit compares the line of action ranges of FA1 and FB1. If the line of action range of FA1 does not overlap with the line of action range of FB1, then at step 650, the control unit determines that no collision has occurred. If the line of action range of FA1 overlaps with the line of action range of FB1, then the analysis moves on to step 651.

At step 651, the control unit compares the directions of the lines of action in the range for force FA1 with the directions of the lines of action in the range for force FB1 in the overlapping region of those ranges. If in the overlapping region of the line of action ranges of the forces FA1 and FB1 there is no line of action in one range which is in an opposing direction to a line of action in the other range, then at step 652 the control unit determines that no collision has occurred. If, however, in the overlapping region of the line of action ranges of the forces FA1 and FB1 there is at least one line of action in one range which is in an opposing direction to a line of action in the other range, then the analysis moves on to step 653.

Alternatively, steps 649 and 651 may be considered together by the control unit rather than separately. In this case, the control unit compares the line of action ranges of FA1 and FB1 including the directions of those lines of action. If there is no overlapping region of the line of action ranges of the forces FA1 and FB1 in which a line of action in one range is in an opposing direction to a line of action in the other range, then the control unit determines that no collision has occurred. If there is an overlapping region of the line of action ranges of the forces FA1 and FB1 in which a line of action in one range is in an opposing direction to a line of action in the other range, then the analysis moves on to step 653.

At step 653, the control unit compares the magnitude range of force FA1 with the magnitude range of force FB1. If the magnitude range of force FA1 does not overlap with the magnitude range of force FB1, then at step 654, the control unit determines that no collision has occurred. If, however, the magnitude range of force FA1 overlaps with the magnitude range of force FB1, then at step 655, the control unit 303 determine that a collision has occurred.

Alternatively, if the magnitude range of force FA1 overlaps with the magnitude range of force FB1, then the control unit 303 may determine that a collision is a possibility. The control unit may then return to steps 640 and 644, and carry out a further iteration of the method described with respect to FIG. 6c. In this iteration, the control unit calculates a narrower range of magnitudes and/or a narrower range of lines of action for a single candidate force which when applied to that arm would cause the residual joint torques. If after this iteration, the magnitude range of force FA1 still overlaps with the magnitude range of force FB1, then the control unit 303 may determine that a collision has occurred. This determination would be with a higher degree of confidence than if the same determination had been made on the previous iteration. Alternatively, the control unit 303 may carry out further iterations of the method of FIG. 6c by returning to steps 640 and 644 each time the answer to step 653 is yes, each subsequent iteration being carried out for a narrower range of magnitudes and/or a narrower range of lines of action than the previous iteration. This iterative process continues until one of the following occurs: (i) the control unit 303 determines that no collision has occurred, or (ii) the ranges are sufficiently narrow that the control unit determines that a collision has occurred. The ranges may be sufficiently narrow after a predetermined number of iterations.

Alternatively, if at step 653, the magnitude range of force FA1 overlaps with the magnitude range of force FB1, then the control unit 303 may determine that a collision is a possibility. The control unit may then employ the method described with respect to FIG. 6a in order to determine whether a collision has occurred or not.

Alternatively, if at step 653, the magnitude range of force FA1 overlaps with the magnitude range of force FB1, then the control unit 303 may determine that a collision is a possibility. The control unit may then employ the method described with respect to FIG. 6b in order to determine whether a collision has occurred or not.

The control unit 303 may stop the collision analysis of FIG. 6c as soon as it determines that no collision has occurred, for example at step 650 if the ranges of the lines of action do not overlap. Alternatively, the collision analysis may continue to compare the other properties of the candidate force described at steps 651 and 653.

The collision analysis described with respect to FIG. 6c in some cases enables the control unit to more quickly dismiss residual joint torques detected on two robot arms as not indicative of a collision than the collision analysis described with respect to FIGS. 6a and 6b.

The above examples described with respect to FIGS. 6a, 6b and 6c explain how the control unit may determine whether a collision has taken place between two robot arms. If the control unit determines that no collision has taken place, then it causes the two robot arms to continue operating as they were prior to the collision assessment. For example, if the control unit was driving the joints of the robot arms to move in response to inputs from the surgeon's console, then the control unit continues to drive the joints in that manner.

If the control unit determines that a collision has taken place, then it may respond by preventing further movement of the two robot arms that have collided. If the robots had been being manipulated in response to inputs from the surgeon's console, preventing movement of the robot arms prevents the surgeon from being able to manipulate the robot arms. The robots may be placed in a compliant mode in which the joints of each robot arm move in response to external forces whilst retaining the instrument in the same location and configuration as it was at the time of the collision. In this manner, operating room staff can push the robot arms to reposition them away from each other. For example, in the compliant mode the control unit may receive sensor input from force sensors on the joints of the robot arm. From this sensor input, the control unit determines that an external force has been applied to the robot arm. The control unit extracts the component of the external force which is in a direction which would move the robot arm away from the collision point. The control unit then drives the robot arm joints to move the robot arm in the direction of that component of the external force. In this approach, the robot arm can only be repositioned by the operating room staff in a manner which would move it away from the collision point with the other robot arm. Once one or both of the robot arms have been repositioned, the control unit may return the robot arms to an operating mode in which they are manipulated in response to inputs from the surgeon's console.

Alternatively, if the control unit determines that a collision has taken place, then it may respond by controlling the robot arms to move away from the point of contact of the two arms. From the collision analysis, the control unit has determined for each robot the line of action of the external force which caused the collision. From the current configurations of the robot arms, the control unit can determine where on each robot arm the force was exerted. The location of the force on each robot arm is the point of contact of that robot arm with the other robot arm.

The control unit may directly respond to a detected collision as described with respect to any one of FIGS. 6a, 6b or 6c by preventing movement of the robot arms or driving the robot arms to back away from the point of contact as described above. Alternatively, the control unit may require one or more further conditions to be met once a collision has been detected in order to react to the detected collision as described.

For example, the control unit may require a threshold force to have been exceeded. In this case, once a collision has been detected, the control unit may compare the magnitude of the candidate force to a threshold force value. If the magnitude of the candidate force exceeds the threshold force value, then the control unit may react to the detected collision as described. If the magnitude of the candidate force does not exceed the threshold force value, then the control unit does not react to the detected collision as described. Instead, the control unit drives the robot arms to continue their normal operation.

In another example, the control unit may require the candidate force to have a particular waveform. For example, the control unit may require the candidate force to exhibit a sharp increase in force indicative of a sudden collision. In this case, once a collision has been detected, the control unit may assess the temporal profile of the candidate force. Specifically, the control unit may assess the gradient of the temporal profile (i.e. magnitude versus time) of the candidate force for the time that the magnitude of the force is greater than a baseline value. If during this time, the temporal profile includes a gradient which is greater than a threshold gradient, then the control unit may react to the detected collision as described. If during this time, the temporal profile does not include a gradient which is greater than a threshold gradient, then the control unit does not react to the detected collision as described. Instead, the control unit drives the robot arms to continue their normal operation.

As another example, the control unit may require the waveform of the candidate force to resemble a step function. The control unit may implement this by, once a collision has been detected (i) assessing whether the magnitude of the candidate force is greater than a baseline value for a time period that is less than a threshold time period, and (ii) assessing whether the temporal profile includes a gradient which is greater than a threshold gradient. If the control unit determines that the magnitude of the candidate force is greater than the baseline value for a time period that is less than the threshold time period, and a gradient of the candidate force is greater than the threshold gradient during that time period, then the control unit may react to the detected collision as described. If during this time, either or both of these requirements is not satisfied, then the control unit does not react to the detected collision as described. Instead, the control unit drives the robot arms to continue their normal operation.

The robotic system may comprise further robots beyond the first and second robots described above. Each further robot has the form described with reference to FIG. 4. The control unit is configured to receive the same sensory data from each further robot and to drive each further robot as described above for the first and second robots. The control unit also performs the above-described collision analysis on each of the further robots. The control unit may require that, in order to react to a detected collision as described above, only two robot arms have residual joint torques which are determined to be caused by balanced and opposing candidate forces. If the control unit determines that three or more robots have residual joint torques which could have been caused by balanced and opposing candidate forces, then the control unit does not react to the detected collision as described. Instead, the control unit drives the robot arms to continue their normal operation.

Collisions are unlikely to occur between more than two robot arms at the same time. If the control unit detects balanced and opposing candidate forces on more than two robot arms, it is likely that the origin of the external force is the patient (which all the robot arms are coupled to as a result of their instruments accessing the surgical site inside the patient) not other robot arms. Thus, the control unit responds to such a finding by enabling the robot arms to continue their normal operation.

The control unit may require any one or combination of these further conditions to be met in order to respond to a detected collision by preventing movement of the robot arms or driving the robot arms to back away from the point of contact as described above. This is so as to reduce the number of false positives from the described collision analysis. In other words, so as to reduce the number of instances in which the control unit detects a collision between robot arms when actually the detected force had another origin. Thus, this reduces the likelihood that the control unit halts the operation and takes control of the surgical instruments away from the surgeon's console when no collision between robot arms had occurred.

Having detected a collision, the control unit may store the configuration of each of the colliding robot arms at the time of the collision in memory 310. In subsequent operation, the control unit prevents the two robot arms from adopting the stored configurations at the same time. The control unit thereby prevents the two robot arms from colliding again in the same manner as the first collision. The control unit does this for the whole of the remaining procedure, or until one or both of the robot bases are moved.

In the event of a collision between two robot arms, an external force is exerted on both the robot arms simultaneously. The magnitude of the force on each robot arm is the same, and the line of action of the force is in opposite directions on the two arms. With knowledge of the geometry of the robot arms and their relative orientation, sensory data from the robot arms can be used to identify the collision as described herein even though the relative positions of the robot arms are not known. Additionally, with knowledge of the geometry of the robot arms and their relative orientation, the control unit can use the detected collision with its known line of action to determine the relative positions of the robot arms. Once the relative positions of the robot arms are known, the control unit can avoid collisions between the robot arms using collision avoidance methods known in the art.

The control unit may perform the collision analysis described herein periodically. Alternatively, the control unit may continually determine residual torques as described with reference to FIG. 5, and every time a residual torque on two robot arms is calculated, perform the collision analysis of one of FIGS. 6a, 6b and 6c. The residual torque on the two robot arms may be required to be greater than a baseline value in order to trigger the subsequent collision analysis.

The position sensors and torque sensors used to provide sensory data to the control unit in the collision analysis described above are not used solely for collision analysis. The position sensors are used for determining the configuration of the robot arm for other purposes. The torque sensors are used for measuring external forces exerted on the robot arms. In a compliant mode of the robot arm, the control unit responds to an external force by driving the robot to move in the direction of the applied external force.

The position sensors could, for example, be potentiometers, optical position encoders, ultrasonic or radio distance sensors. The force sensors could, for example, be resistance-based strain gauges, piezoelectric strain gauges, optical strain gauges or semiconductor strain gauges. The drivers for driving the joints of the robot to move could be rotary or linear motors, or means other than motors: for example hydraulic or pneumatic rams.

The robot could be used for purposes other than surgery. For example, the robot could be used in car manufacturing for viewing the inside of an engine.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A surgical robotic system comprising:
   a first surgical robot and a second surgical robot, each surgical robot having a base, and an arm extending from the base to an attachment configured to attach an instrument, the arm comprising a plurality of joints whereby the configuration of the arm can be altered, for each joint the surgical robot comprising a driver configured to drive the joint to move, and a position sensor and torque sensor configured to sense the joint; and
   a control unit configured to receive inputs from the position sensors and torque sensors, and to control the drivers in dependence on those received inputs, the control unit configured to:
   determine the gravitational torques on the joints of the arms of the first and second surgical robots in the arm configurations indicated from the inputs from the position sensors;
   from the inputs from the torque sensors and the determined gravitational torques, determine residual torques on the joints of the arms of the first and second surgical robots in the indicated arm configurations;
   calculate one or more candidate force for each arm which when applied to that arm would cause the determined residual torques; and
   determine a collision if one or more candidate force on the arm of the first surgical robot balances an opposing candidate force on the arm of the second surgical robot.

2. A surgical robotic system as claimed in claim 1, the control unit being configured to, on determining a collision, control the drivers so as to prevent the arms of the first and second surgical robot from moving.

3. A surgical robotic system as claimed in claim 2, wherein the control unit is configured to control the drivers as claimed only if the candidate force exceeds a threshold force.

4. A surgical robotic system as claimed in claim 2, wherein the control unit is configured to control the drivers as claimed only if the temporal profile of the candidate force has a gradient greater than a threshold gradient.

5. A surgical robotic system as claimed in claim 2, wherein the control unit is configured to control the drivers as claimed only if the candidate force has a magnitude greater than a baseline value for a time period that is less than a threshold time period.

6. A surgical robotic system as claimed in claim 2, comprising further surgical robots, each further surgical robot having a base, and an arm extending from the base to an attachment configured to attach an instrument, the arm comprising a plurality of joints whereby the configuration of the arm can be altered, for each joint the surgical robot comprising a driver configured to drive the joint to move, and a position sensor and torque sensor configured to sense the joint, the control unit configured to:
   determine the gravitational torques on the joints of the arms of the further surgical robots in the arm configurations indicated from the inputs from the position sensors;
   from the inputs from the torque sensors and the determined gravitational torques, determine residual torques on the joints of the arms of the further surgical robots in the indicated arm configurations;
   calculate one or more candidate force for each arm of the further surgical robots which when applied to that arm would cause the determined residual torques; and
   control the drivers as claimed only if a collision is determined and the candidate force on the arm of the first surgical robot which balances an opposing candidate force on the arm of the second surgical robot does not also balance an opposing candidate force on the arm of a further surgical robot.

7. A surgical robotic system as claimed in claim 1, the control unit being configured to, on determining a collision, control the drivers to move the arms of the first and second surgical robot away from the point of contact.

8. A surgical robotic system as claimed in claim 1, wherein the control unit is configured to store the configuration of the arm of the first surgical robot and the configuration of the arm of the second surgical robot at the time of the determined collision, and subsequently prevent the first surgical robot and the second surgical robot from both adopting those stored configurations at the same time.

9. A surgical robotic system as claimed in claim 1, wherein the control unit is configured to determine the relative position of the arm of the first surgical robot and the arm of the second surgical robot from the determined collision, and subsequently prevent the arm of the first surgical robot and the arm of the second surgical robot from adopting the same relative position at the same time.

10. A surgical robotic system as claimed in claim 1, wherein the control unit is configured to operate as claimed without knowledge of the relative positions of the first surgical robot and the second surgical robot.

11. A surgical robotic system as claimed in claim 1, wherein the control unit is configured to assume that the first and second surgical robots each adopt a predetermined orientation with respect to each other.

12. A surgical robotic system as claimed in claim 1, wherein the control unit is configured to calculate only a single candidate force for each arm which when applied to that arm would cause the determined residual torques.

13. A surgical robotic system as claimed in claim 12, wherein the control unit is configured to determine that no collision has taken place if there is no single candidate force which when applied to the arm of the first surgical robot would cause the determined residual torques on the joints of the arm of the first surgical robot in the indicated arm configuration.

14. A surgical robotic system as claimed in claim 1, wherein the control unit is configured to calculate only a single candidate force range for each arm which when applied to that arm would cause the determined residual torques.

15. A surgical robotic system as claimed in claim 14, wherein the single candidate force range comprises a candidate magnitude range and a candidate line of action range.

16. A surgical robotic system as claimed in claim 15, wherein the control unit is configured to determine that no collision has taken place if the candidate line of action range of the arm of the first surgical robot does not overlap with the candidate line of action range of the arm of the second surgical robot.

17. A surgical robotic system as claimed in claim 15, wherein the control unit is configured to determine that no collision has taken place if the candidate line of action range of the arm of the first surgical robot does not include a line of action in an opposing direction to a line of action in the candidate line of action range of the arm of the second surgical robot.

18. A surgical robotic system as claimed in claim 15, wherein the control unit is configured to determine that no collision has taken place if the candidate magnitude range of the arm of the first surgical robot does not overlap with the candidate magnitude range of the arm of the second surgical robot.

19. A surgical robotic system as claimed in claim 1, wherein the control unit is configured to determine, for each arm, a plurality of candidate forces, each of which when applied to that arm would cause the determined residual torques, the plurality of candidate forces including combination candidate forces, combination candidate forces being a combination of two or more individual candidate forces, the control unit being configured to determine a collision if an individual candidate force of a combination candidate force on the arm of the first surgical robot balances an opposing candidate force on the arm of the second surgical robot.

20. A method of determining collisions between a first surgical robot and a second surgical robot of a surgical robotic system, each surgical robot having a base, and an arm extending from the base to an attachment configured to attach an instrument, the arm comprising a plurality of joints whereby the configuration of the arm can be altered, for each joint the surgical robot comprising a driver configured to drive the joint to move, and a position sensor and torque sensor configured to sense the joint, the surgical robotic system further comprising a control unit configured to receive inputs from the position sensors and torque sensors and configured to control the drivers in dependence on those received inputs, the method comprising:
   determining the gravitational torques on the joints of the arms of the first and second surgical robots in the arm configurations indicated from the inputs from the position sensors;
   from the inputs from the torque sensors and the determined gravitational torques, determining residual torques on the joints of the arms of the first and second surgical robots in the indicated arm configurations;
   calculating one or more candidate force for each arm which when applied to that arm would cause the determined residual torques; and
   determining a collision if one or more candidate force on the arm of the first surgical robot balances an opposing candidate force on the arm of the second surgical robot.

* * * * *